United States Patent
Tobert

(10) Patent No.: US 6,673,831 B1
(45) Date of Patent: Jan. 6, 2004

(54) COMBINATION THERAPY FOR REDUCING THE RISKS ASSOCIATED WITH CARDIOVASCULAR DISEASE

(75) Inventor: Jonathan A. Tobert, Maplewood, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/067,432

(22) Filed: Apr. 27, 1998

Related U.S. Application Data

(63) Continuation of application No. 08/839,483, filed on Apr. 14, 1997, now abandoned.
(60) Provisional application No. 60/020,977, filed on Jun. 24, 1996, and provisional application No. 60/015,689, filed on Apr. 17, 1996.

(51) Int. Cl.[7] .................. A61K 31/35; A61K 31/505
(52) U.S. Cl. ....................... 514/455; 514/260
(58) Field of Search .................. 514/455, 260

(56) References Cited

U.S. PATENT DOCUMENTS

| 3,895,107 A | 7/1975 | Morrison |
| 5,084,482 A | 1/1992 | Hirsch et al. |
| 5,470,845 A * | 11/1995 | Magnin et al. ............. 514/121 |
| 5,631,401 A | 5/1997 | Stein et al. |

FOREIGN PATENT DOCUMENTS

| DE | 232 580 9 | 12/1974 |
| DE | 235 729 9 | 5/1975 |
| DE | 43 26 698 | 3/1995 |
| WO | 43 26 698 A 1 | 3/1995 |

OTHER PUBLICATIONS

Hopkins et al.; "Folic acid may protect patients with early heart disease"; American Heart Association News Release No. NR 95–4320, Sep. 11, 1995.*
Dobs, A. et al., "Lipid–lowering Diets in patients taking pravastatin, a new HMG–CoA reductase inhibitor: compliance and adequacy", American Journal of Clinical Nutrition, vol 54, No. 4, pp. 696–700, 1991.
Frohlich, et al., "Lipoproteins and homocyst(e)ine as risk factors for atherosclerosis: Assessment and treatment", Canadian Journal of Cardiology, vol. 11, pp. 18C–23C, 1995.
The Merck Manual of Diagnosis and Therapy, 16th Edition, pp. 1044–1045, 1992.
Boushey, et al., "A Quantitiative Assessment of Plasma Homocysteine as a Risk Factor For Vascular Disease", JAMA, vol. 274, No. 13, pp. 1049–1057, 1995.
Mayer, et al., "Homocysteine and Coronary Atherosclerosis", Journal of The American College of Cardiology, vol. 27, No. 3, pp. 517–527, 1996.

Feher, et al., "Long–term safety of statin–fibrate combination treatment in the management of hypercholesterolaemia in patients with coronary artery disease", British Heart Journal, British Medical Association, vol. 74, No. 1, pp. 14–17, 1995.
Tonstad, et al., "Low dose colestipol in adolescents with familial hypercholesterolaemia", Archives of Disease in Childhood, vol. 74, No. 2, pp. 157–160, 1996.
Hopkins et al., "Folic acid amay protect patients with early heart disease"; American Heart Association News Release No. NR 95–4320 (Sep. 11, 1995).
Ubbink et al., "Vitamin Requirements for the Treatment of Hyperhomocysteinemia in Humans", J. Nutr., vol. 124 (10), pp. 1927–1933 (Oct. 1994).
Robinson et al., "Homocysteine and coronary artery disease", Cleve. Clin. J. Med., vol. 61 (6), pp. 438–450 (Nov.–Dec. 1994).
M. Rene Malinow, "Plasma Homocysteine and arterial occlusive disease: a mini review", Clin Chem., vol. 41(1), pp. 173–176 (Jan. 1995).
Van Den Berg et al., "Hyperhomocysteinaemia and endothelial dysfunction in young patients . . . ", Eur. J. Clin. Invest, vol 25, pp. 176–181 (1995).
Brattstrom et al, "Homocysteine and cysteine: determinants of plasma levels in middle aged and elderly subjects", J. Intern. Med., vol. 236(6), pp. 633–641 (1994).
Stampfer et al., "Can lowering homocysteine levels reduce cardiovascular risk?", N. Eng. J. of Med., vol. 332(5), pp. 328–329 (Feb. 1995).
Dudman et al., "Disordered methionine/homocysteine metabolism in premature vaascular disease", Arteriosclerosis and Thrombosis, vol. 13(9), pp. 1253–1260 (Sep. 1993).
Glueck et al., "Evidence that homocysteine is an independent risk factor for atherosclerosis in hyperlipidemic patients", Amer. J. Cardiology, vol. 75(2), pp. 132–136 (Jan. 1995).
Dalery et al., "Homocysteine and coronary artery disease in French Canadian subjects . . . ", Amer. J. Cardiology, vol. 75(16), pp. 1107–1111 (Jun. 1995).
Pancharuniti et al, "Plasma homocysteine, folate and vitamin B–12 concentrations and risk for early onset coronary artery disease", Amer. J. Clin. Nutr., vol. 59(4), pp. 940–948 (Apr. 1994).
Ubbink et al., "Vitamin B–12, vitamin B–6 and folate nutritional status in men with hyperhomocysteinemia", Amer. J. Clin. Nutr., vol. 57(1), pp. 47–53 (Jan. 1993).

(List continued on next page.)

Primary Examiner—Theodore J. Criares
(74) Attorney, Agent, or Firm—Carol S. Quagliato; Melvin Winokur

(57) ABSTRACT

The instant invention provides methods for preventing or reducing the risk of developing atherosclerosis, as well as for halting or slowing the progression of atherosclerotic disease once it has become clinically evident, comprising the administration of a therapeutically effective amount of an HMG-CoA RI in combination with folic acid or a pharmaceutically acceptable salt or ester thereof to a person who is at risk of developing atherosclerosis or who already has atherosclerotic disease.

29 Claims, No Drawings

OTHER PUBLICATIONS

G. H. J. Boers, "Hyperhomocysteinaemia: a nely recongized risk factor for vascular disease", Netherlands J. Medicine, vol. 45(1), pp. 34–41 (Jul. 1994).

Giles et al., "Serum folate and risk for ischemic stroke. First national Health and Nutrition Examination Survey Epidemiologic follow–up study", Stroke, vol. 26(7), pp. 1166–1170 (Jul. 1995).

van den Berg et al., "Combined vitamin B6 plus folic acid therapy in young patients with ateriosclerosis and hyperhomocysteinemia", J. Vascular Surgery, vol. 20(6), pp. 933–940 (Dec. 1994).

Franken et al., "Treatment of mild Hyperhomocysteinemia in vascular disease patients", Arteriosclerosis and Thrombosis, vol. 14(3), pp. 465–470 (Mar. 1994).

Bergmark et al., "Hyperhomocysteinemia in patients operation for lower extremity Ischaemia . . . ", Eur. J. Vascular Surgery, vol. 7(4), pp. 391–396 (Jul. 1993).

Boushey et al., "A Quantitative Assessment of Plasma Homocysteine as a Risk Factor for Vascular Disease", JAMA, vol. 274(13), pp. 1049–1057 (Oct. 1995).

Nygard et al., "Total Plasma Homocysteine and Cardiovascular Risk Profile", JAMA, vol. 274 (19), pp. 1526–1532 (Nov. 1995).

Perry et al., "Prospective study of serum total homocysteine concentration and risk of stroke . . . ", The Lancet, vol. 346, pp. 1395–1398 (Nov. 1995).

Nygard et al., "Plasma Homocysteine Levels and Mortality in Patients with Coronary Artery Disease", New England J. Of Med., vol. 337, pp. 230–236 (Jul. 1997).

Tucker et al., "Folic acid fortification of the food supply", JAMA, vol. 276(23), pp. 1879–1885 (Dec. 1996).

N. R. C. Campbell., "How safe are folic acid supplements?", Arch. Intern. Med., vol. 156, pp. 1638–1644 (Aug. 1996).

A. Dobs et al., "Lipid–lowering diets in patients taking pravastatin, a new HMG–CoA reductase inhibitor; compliance and adequacy", Amer. J. of Clin Nutrition, vol. 54(4), pp. 696–700 (1991).

Frolich et al., "Lipoproteins and homocysteine as risk factors for artherosclerosis: Assessment and treatment", Cana. J. of Cardiology, vol. 11, Supp. C, pp. 18C–23C, (1995).

The merck Manual of Diagnosis and Therapy, 16th edition, pp. 1044–1045 (1992).

Mayer et al., "Homocysteine and Coronary Atherosclerosis", J. of the American College of Cardiology, vol. 27(3), pp. 517–527 (1996)

Feher et al., "Long–term safety of statin–fibrate combination treatment in the management of hypecholesterolaemia in patients with coronary artery disease", British Heart Journal, British Medical Association, vol. 74(1), pp. 14–17 (1996).

Tonstad et al., "Low dose colestipol in adolescents with familial gypecholesterolaemia", Archives of Disease in childhood, vol. 74(2), pp. 157–160 (1996).

MacMahon et al., "A pilot study with simvastatin and folic acid/vitamin B12 in preparation for the Study of Effectiveness of Additional Reductions in Cholesterol and Homocysteine (SEARCH)", Nutr. Metab. Cardiovasc. Dis., vol. 10, pp. 195–203 (2000).

* cited by examiner

COMBINATION THERAPY FOR REDUCING THE RISKS ASSOCIATED WITH CARDIOVASCULAR DISEASE

RELATED APPLICATIONS

This application is a continuation of U.S. Ser. No. 08/839,483, filed Apr. 14, 1997, now abandoned which itself claims priority to U.S. provisional application No. 60/020,977, filed Jun. 24, 1996, and U.S. provisional No. 60/015,689, filed Apr. 17, 1996.

BACKGROUND OF THE INVENTION

The instant invention involves a combination therapy comprising the administration of a 3-hydroxy-3-methylglutaryl coenzyme A (HMG-CoA) reductase inhibitor (or HMG-CoA RI) and folic acid or a pharmaceutically acceptable salt or ester thereof for preventing, halting or slowing the progression of atherosclerotic cardiovascular diseases and related conditions and disease events.

There is increasing evidence that high blood levels of homocysteine are associated with an increased risk of coronary heart disease (CHD) and stroke. The mechanism of the association is unknown, but it is well established that folic acid (a B complex vitamin) lowers plasma homocysteine by increasing its catabolism.

It has been clear for several decades that elevated blood cholesterol is a major risk factor for coronary heart disease, and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events.

Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

The use of folic acid to reduce the risk of cardiovascular disease by reducing homocysteine levels is attractive as this therapy is believed to be almost risk-free (folic acid is a vitamin) and relatively inexpensive. In addition, as the dose of folic acid required to reduce homocysteine is small (typically 1–5 mg daily) and, like HMG-CoA reductase inhibitors, may be given once daily, the active agents can be readily combined in a single tablet, capsule or other dosage form having the same or similar size as the inhibitor of HMG-CoA reductase alone. This would provide patient convenience, an important consideration especially in patients who already have coronary heart disease, as such patients generally have several different drugs to take.

SUMMARY OF THE INVENTION

The instant invention involves a novel combination therapy comprised of a therapeutically effective amount of an HMG-CoA reductase inhibitor in combination with folic acid or a pharmaceutically acceptable salt or ester thereof.

One object of the instant invention is to administer the above-described combination therapy to people who do not yet show clinical signs of atherosclerosis, but who are at risk of developing atherosclerosis and associated diseases. Clinical manifestations of atherosclerosis include atherosclerotic cardiovascular disease such as coronary heart disease (also known as ischemic heart disease), cerebrovascular disease, and peripheral vessel disease. Toward this end, the instant invention provides methods for preventing or reducing the risk of developing atherosclerotic cardiovascular disease, coronary heart disease, cerebrovascular disease and peripheral vessel disease, and preventing or reducing the risk of occurrence, or recurrence where the potential exists, of a coronary heart disease event, a cerebrovascular event, and/or intermittent claudication, by administering the above-described combination therapy to said at-risk persons.

A second object of the instant invention is to provide the above-described combination therapy to people who have clinical signs of atherosclerosis. Toward this end, the instant invention provides methods for halting or slowing the progression of atherosclerotic cardiovascular disease, coronary heart disease, ischemic heart disease, cerebrovascular disease and peripheral vessel disease, and preventing or reducing the risk of occurrence, or recurrence where the potential exists, of a coronary heart disease event, a cerebrovascular event, and/or intermittent claudication, by administering the above-described combination therapy to said persons who have clinically manifest atherosclerotic disease.

A third object of the instant invention involves the above-described methods further comprising the administration of one or more additional active agents, for example, a bile acid sequestrant, cholesterol absorption inhibitor, squalene synthase inhibitor, and/or niacin, either in separate or combined dosage formulations. A fourth object is to provide pharmaceutical compositions which can be used in the above-described methods. Additional objects will be evident from the following detailed description.

DETAILED DESCRIPTION OF THE INVENTION

The instant invention provides methods for preventing or reducing the risk of developing atherosclerosis, as well as for halting or slowing the progression of atherosclerotic disease once it has become clinically evident, comprising the administration of a therapeutically effective amount of an HMG-CoA RI in combination with folic acid or a pharmaceutically acceptable salt or ester thereof to a person who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease."

The combination comprised of an HMG-CoA RI and folic acid or folate may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompasses coronary heart disease events, cerebrovascular events, and intermittent claudication. It is intended that persons who have previously experienced one or more non-fatal atherosclerotic disease event are those for whom the potential for recurrence of such an event exists.

Accordingly, the instant invention also provides a method for preventing or reducing the risk of occurrence, or recurrence where the potential exists, of an atherosclerotic disease event comprising the administration of a therapeutically effective amount of an HMG-CoA reductase inhibitor in combination with folic acid or folate to a person at risk of developing atherosclerotic disease. The instant combination therapy can also be administered to a person who already has atherosclerotic disease for preventing or reducing the risk of occurrence, or recurrence where the potential exists, of an atherosclerotic disease event.

Persons to be treated with the instant combination therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: National Cholesterol Education Program, Second report of the Expert Panel on *Detection, Evaluation, and Treatment of High Blood Cholesterol in Adults* (*Adult Treatment Panel II*), National Institute of Health, National Heart Lung and Blood Institute, NIH Publication No. 93-3095, September 1993; abbreviated version: Expert Panel on Detection, Evaluation, and Treatment of High Blood Cholesterol in Adults, *Summary of the second report of the national cholesterol education program* (*NCEP*) *Expert Panel on Detection, Evaluation, and Treatment of High Blood Cholesterol in Adults* (*Adult Treatment Panel II*), *JAMA*, 1993, 269, pp. 3015–23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

A compound which inhibits HMG-CoA reductase is used in combination with folic acid or folate to practice the instant invention. Examples of HMG-CoA reductase inhibitors that may be used include but are not limited to lovastatin (MEVACOR®), simvastatin (ZOCOR®), pravastatin (PRAVACHOL®), fluvastatin (LESCOL®), atorvastatin and rivastatin (also known as cerivastatin). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996). The term HMG-CoA reductase inhibitor is intended to include all pharmaceutically acceptable salt and ester forms of compounds which have HMG-CoA reductase inhibitory activity, and therefor the use of such salts and esters is included within the scope of this invention.

Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. Preferably, the HMG-CoA RI is selected from lovastatin and simvastatin.

Folic acid or a pharmaceutically acceptable salt or ester thereof is administered in combination with the HMG-CoA reductase inhibitor. Pharmaceutically acceptable salts of folic acid are well known to those skilled in the art and include, for example, the sodium salt and the methylglucamine salt. The acid moiety also lends itself to the preparation of pharmaceutically acceptable esters, and such esters are likewise included in the scope of the invention. The term "folate" is used herein to refer to the pharmaceutically acceptable salts and esters of folic acid.

Herein, the term "pharmaceutically acceptable salts" shall mean non-toxic salts of the compounds employed in this invention which are generally prepared by reacting the free acid with a suitable organic or inorganic base.

Ester derivatives of the described compounds may act as prodrugs which, when absorbed into the bloodstream of a warm-blooded animal, may cleave in such a manner as to release the drug form and permit the drug to afford improved therapeutic efficacy.

The instant method involves the administration of an HMG-CoA reductase inhibitor in combination with folic acid or a folate. This combination therapy includes administration of a single pharmaceutical dosage formulation which contains both the HMG-CoA reductase inhibitor and the folic acid or folate, as well as administration of each active agent in its own separate pharmaceutical dosage formulation. Where separate dosage formulations are used, the HMG-CoA reductase inhibitor and the folic acid or folate can be administered at essentially the same time, i.e., concurrently, or at separately staggered times, i.e, sequentially. It is preferred that the HMG-CoA reductase inhibitor and the folic acid or folate be co-administered concurrently on a once-a-day dosing schedule. A single dosage formulation comprised of both an HMG-CoA reductase inhibitor and the folic acid or folate is preferred. A single dosage formulation will provide convenience for the patient, which is an important consideration especially for patients who already have coronary heart disease and may be in need of multiple medications.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The dosage regimen utilizing an HMG-CoA RI in combination with folic acid or folate is selected in accordance with a variety of factors including type, species, age, weight, sex and medical condition of the patient; the severity of the condition to be treated; the route of administration; the renal and hepatic function of the patient; and the particular compound or salt or ester thereof employed. A consideration of these factors is well within the purview of the ordinarily skilled clinician for the purpose of determining the therapeutically effective dosage amounts to be given to a person in need of the instant combination therapy. Dosage information for HMG-CoA RI's and for folic acid is well known in the art, since several HMG-CoA RI's and nutritional supplements containing folic acid are marketed in the U.S.

In particular, the daily dosage amounts of the HMG-CoA reductase inhibitor are intended to be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA RI is from about 1 to 200 mg/day, and more preferably from about 5 to 160 mg/day. However, dosage amounts will vary depending on the potency of the specific HMG-CoA reductase inhibitor used as well as other factors as noted above. An HMG-CoA RI which has sufficiently greater potency may be given in sub-milligram daily dosages.

As examples, the daily dosage amount for simvastatin may be selected from 5 mg, 10 mg, 20 mg, 40 mg, 80 mg and 160 mg; for lovastatin, 10 mg, 20 mg, 40 mg and 80 mg; for fluvastatin sodium, 20 mg, 40 mg and 80 mg; and for pravastatin sodium, 10 mg, 20 mg, and 40 mg.

The therapeutically effective amount of folic acid to be used in the instant method is intended to be a dosage amount sufficient to reduce the plasma level of homocysteine below the pre-treatment plasma level of homocysteine in the person receiving the combination therapy. Examples of dosage amounts of folic acid are described in the PDR. For example, see at page 119 of the 1996 PDR the heading "Folic Acid" and the reference pages cited therein. For example, the daily dosage amount of folic acid or folate employed in the instant combination therapy can be from about 0.1 to 20 mg/day. In particular, the dosage is from about 0.1 to 10 mg/day, more particularly from about 0.1 to 5 mg/day, and most particularly from about 1 to 5 mg/day, based on the free acid weight. For example, the daily dosage amount of folic acid or folate may be selected from 1 mg, 2 mg and 5 mg, based on the free acid weight.

Additional active agents may be combined with the HMG-CoA RI and folic acid or folate in a single dosage formulation, or may be administered to the patient in a separate dosage formulation, which allows for concurrent or sequential administration. One or more additional active agents may be administered with the HMG-CoA RI and folic acid or folate. The additional active agent or agents can be cholesterol lowering compounds. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); aspirin; beta-blockers; and anti-oxidant vitamins such as vitamin C and E and beta carotene.

Examples of HMG-CoA synthase inhibitors include: the beta-lactone derivatives disclosed in U.S. Pat. Nos. 4,806, 564, 4,816,477, 4,847,271, and 4,751,237; the beta lactam derivatives disclosed in U.S. Pat. No. 4,983,597 and the substituted oxacyclopropane analogues disclosed in European Patent Publication EP 0 411 703. The squalene synthetase inhibitors suitable for use herein include, but are not limited to, those disclosed by Biller et al., *J. Med. Chem.*, 1988 Vol. 31, No. 10, pp. 1869–1871, including isoprenoid (phosphinylmethyl)-phosphonates such as those of the formula

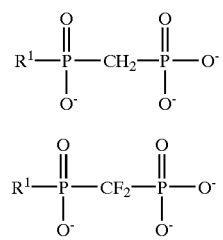

wherein $R^1$ is:

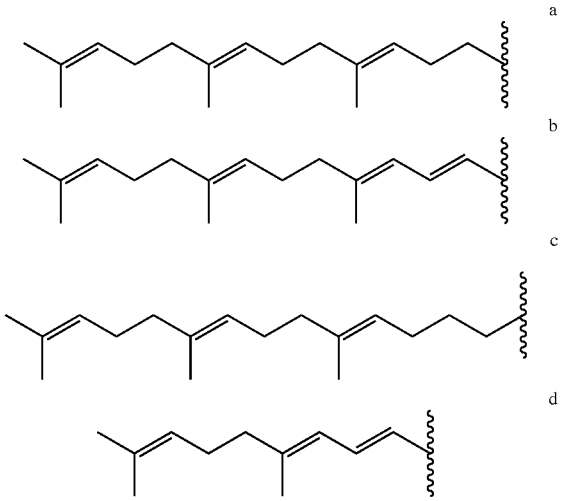

including the triacids thereof, triesters thereof and tripotassium and trisodium salts thereof as well as other squalene synthetase inhibitors disclosed in pending U.S. Pat. Nos. 4,871,721 and 4,924,024 and in Biller et al., *J. Med. Chem.*, 1988, Vol. 31, No. 10, pp. 1869 to 1871.

In addition, other squalene synthetase inhibitors suitable for use herein include the terpenoid pyrophosphates disclosed by P. Ortiz de Montellano et al., *J. Med. Chem.*, 1977, 20, 243–249, the farnesyl diphosphate analog A and presqualene pyrophosphate (PSQ-PP) analogs as disclosed by Corey and Volante, *J. Am. Chem. Soc.* 1976, 98, 1291–1293, phosphinylphosphonate reported by McClard, R. W. et al., *J.A.C.S.*, 1987, 109, 5544 and cyclopropanes reported by Capson, T. L., PhD dissertation, June, 1987, *Dept. Med. Chem. U. of Utah*, Abstract, Table of Contents, pp. 16, 17, 40–43, 48–51, Summary.

Further, the benzodiazepine squalene synthase inhibitors described in EP 0 567 026 to Takeda Chemical Industries, and the quinuclidinyl squalene synthase inhibitors described in PCT publications WO 94/03451, WO 93/09115, WO 93/21183, WO 93/21184, WO 93/24486, and U.S. Pat. No. 5,135,935, may be co-administered with the HMG-CoA RI plus folic acid or folate combination of the present invention. In addition, the zaragozic acid type squalene synthase inhibitors as described in U.S. Pat. Nos. 5,284,758; 5,283,256; 5,262,435; 5,260,332; 5,264,593; 5,260,215; 5,258,401; 5,254,727; 5,256,689; 5,132,320; 5,278,067, and PCT Publications WO 92/12156; WO 92/12157; WO 92/12158; WO 92/12159; WO 92/12160; WO 93/18040; WO 93/18039; WO 93/07151; and European Patent Publications EP 0 512 865, EP 0 568 946; EP 0 524,677 and EP 0 450 812, as well as the acyclic tricarboxylic acid compounds of U.S. Pat. No. 5,254,727, may be employed.

Illustrative examples of squalene epoxidase inhibitors are disclosed in European Patent Publication EP 0 318 860 and in Japanese Patent Publication JO2 169-571A. LDL-receptor gene inducer molecules are disclosed in U.S. Pat. No. 5,182,298.

Examples of bile acid sequestrants which may be employed in the present method include cholestyramine, colestipol, and poly[methyl-(3-trimethylaminopropyl) imino-trimethylene dihalide] and those disclosed in W095/34585 to Geltex Pharmaceuticals, Inc. and EP 0 622 078 assigned to Hisamitsu Pharmaceutical Co., Inc.

Examples of cholesterol absorption inhibitors which may be employed in the present method include those described in WO 95/18143 and WO 95/18144 both assigned to Pfizer Inc., and WO 94/17038, WO 95/08532 and WO 93/02048 each assigned to Schering Corp.

The additional active agents described above which may be employed along with the HMG-CoA RI and folic acid or folate combination therapy can be used, for example, in amounts as indicated in the PDR or in amounts as indicated in the reference disclosures, as appropriate.

Pharmaceutical formulations for both HMG-CoA RI's and for folic acid or folates are well-known to those skilled in the art, as evidenced by the information provided in the 1996 PDR. Methods for preparing various pharmaceutical compositions comprising the combination of an HMG-CoA RI and folic acid or folate are likewise well known to those skilled in the art. For example, see *Remington's Pharmaceutical Sciences*, Mack Publishing Co., Easton, Pa.

For example, the active agents employed in the instant combination therapy can be administered in such oral forms as tablets, capsules (each of which includes sustained release or timed release formulations), pills, powders, granules, elixirs, tinctures, suspensions, syrups, and emulsions. The instant invention includes the use of both oral rapid-release and time-controlled release pharmaceutical formulations. Oral formulations are preferred.

In the methods of the present invention, the HMG-CoA RI and the folic acid or folate may be formulated together with or without an additional active agent, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants (BHA, BHT, propyl gallate, sodium ascorbate, citric acid) can also be added to stabilize the dosage forms. Other suitable components include gelatin, sweeteners, natural and synthetic gums such as acacia, tragacanth or alginates, carboxymethylcellulose, polyethylene glycol, waxes and the like.

Although the active agents of the present method may be administered in divided doses, for example two or three times daily, a single daily dose of each of the HMG-CoA RI and the folic acid or folate is preferred, with a single daily dose of both agents in a single pharmaceutical composition being most preferred.

As such, a therapeutically effective amount of an HMG-CoA RI and folic acid or a pharmaceutically acceptable salt or ester thereof can be used together for the preparation of a medicament useful for preventing or reducing the risk of developing atherosclerotic disease, halting or slowing the progression of atherosclerotic disease once it has become clinically manifest, and preventing or reducing the risk of occurrence, or recurrence where the potential exists, of an atherosclerotic disease event. For example, the medicament may be comprised of folic acid or folate in combination with about 1 mg to 200 mg of an HMG-CoA RI, or more particularly about 5 mg to 160 mg of the HMG-CoA RI. More specific amounts of HMG-CoA RI which may be used in the medicament preparation include 1 mg, 5 mg, 10 mg, 20 mg, 40 mg, 80 mg, and 160 mg, as well as sub-milligram amounts of HMG-CoA RI's which have sufficient potency at such levels. As a further example, the medicament may be comprised of an HMG-CoA RI in combination with about 0.1 to 20 mg of folic acid or folate. In particular, the amount of folic acid or folate used in the preparation of the medicament may be from about 0.1 to 10 mg, or more particularly from about 0.1 to 5 mg, and most particularly from about 1 to 5 mg, based on the free acid weight. For example, the medicament may be comprised of 1 mg, 2 mg or 5 mg of folic acid or folate, based on the free acid weight.

The above-described medicament may also be prepared with one or more additional active agents such as an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequesterant, an LDL receptor inducer, vitamin $B_6$ and the pharmaceutically acceptable salts thereof, vitamin $B_{12}$, aspirin, beta-blockers, vitamin C, vitamin E and beta carotene.

An example of an oral dosage formulation comprising both an HMG-CoA RI and folic acid which is suitable for use in practicing the instant method invention is as follows:

| Ingredient | Amount |
|---|---|
| simvastatin | 1–200 mg. |
| folic acid or folic acid equivalent | 0.05–20 mg. |
| diluent<br>binder<br>disintegrant<br>lubricant } excipients | qs. 200–400 mg. |

More specific examples of oral dosage formulations are as follows.

EXAMPLE 1

| Ingredient | Amount |
|---|---|
| Simvastatin | 5.0 mg |
| BHA | 0.02 mg |
| Ascorbic acid | 2.50 mg |
| Citric acid | 1.25 mg |
| Microcrystalline cellulose | 5.0 mg |
| Pregel starch | 10.0 mg |
| Magnesium stearate | 0.5 mg |
| Lactose | 74.73 mg |
| Folic acid | 1.0 mg |

All the ingredients except magnesium stearate are blended together in a suitable mixer. The powder mixture is then granulated with adequate quantities of granulating solvent(s). The wet granulated mass is dried in a suitable dryer. The dried granulation is sized through a suitable screen. The sized granulation is mixed with magnesium stearate before tableting. The tablets may be coated if deemed necessary. Additional ingredients that may be added to the above include suitable color and mixtures of colors.

EXAMPLE 2

| Ingredient | Amount |
|---|---|
| Simvastatin | 5.0 mg |
| BHA | 0.04 mg |
| Citric acid | 2.5 mg |
| Microcrystalline cellulose | 10.0 mg |
| Pregel starch | 20.0 mg |
| Magnesium stearate | 1.0 mg |
| Lactose | 148.46 mg |
| Folic acid | 5.0 mg |
| Hydrolized gelatin | 8.0 mg |

The process of manufacture is essentially the same as in Example 1, above.

EXAMPLE 3

| Ingredient | Amount |
|---|---|
| Simvastatin | 80.0 mg |
| BHA | 0.16 mg |
| Ascorbic acid | 20.0 mg |
| Citric acid | 10.0 mg |
| Microcrystalline cellulose | 40.0 mg |
| Pregel starch | 80.0 mg |
| Lactose | 550.0 mg |
| Folic acid | 10.0 mg |
| Colorant | 5.0 mg |
| Magnesium stearate | 4.8 mg |

The process of manufacture is essentially the same as in Example 1, above.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for preventing or reducing the risk of developing atherosclerotic disease comprising the administration of a therapeutically effective amount of an HMG-CoA reductase inhibitor in combination with folic acid or a pharmaceutically acceptable salt or ester thereof to a person at risk of developing atherosclerotic disease.

2. The method of claim 1 wherein the atherosclerotic disease is selected from cardiovascular disease, cerebrovascular disease and peripheral vessel disease.

3. The method of claim 2 wherein the cardiovascular disease is coronary heart disease.

4. The method of claim 1 wherein the HMG-CoA reductase inhibitor is selected from lovastatin, simvastatin, pravastatin, fluvastatin, atorvastatin, rivastatin and the pharmaceutically acceptable salts and esters thereof.

5. The method of claim 4 wherein the HMG-CoA reductase inhibitor is selected from lovastatin and simvastatin.

6. The method of claim 1 wherein the pharmaceutically acceptable salt of folic acid is selected from the sodium salt and the methylglucamine salt.

7. The method of claim 1 further comprising the administration of a therapeutically effective amount of an active agent selected from an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequestrant, an LDL receptor inducer, vitamin $B_6$ and the pharmaceutically acceptable salts thereof, vitamin $B_{12}$, aspirin, a beta-blocker, vitamin C, vitamin E and beta carotene.

8. A method for halting or slowing the progression of atherosclerotic disease comprising the administration of a therapeutically effective amount of an HMG-CoA reductase inhibitor in combination with folic acid or a pharmaceutically acceptable salt or ester thereof to a person who has atherosclerotic disease.

9. The method of claim 8 wherein the atherosclerotic disease is selected from cardiovascular disease, cerebrovascular disease and peripheral vessel disease.

10. The method of claim 9 wherein the cardiovascular disease is coronary heart disease.

11. The method of claim 8 wherein the HMG-CoA reductase inhibitor is selected from lovastatin, simvastatin, pravastatin, fluvastatin, atorvastatin, rivastatin and the pharmaceutically acceptable salts and esters thereof.

12. The method of claim 11 wherein the HMG-CoA reductase inhibitor is selected from lovastatin and simvastatin.

13. The method of claim 8 wherein the pharmaceutically acceptable salt of folic acid is selected from the sodium salt and the methylglucamine salt.

14. The method of claim 8 further comprising the administration of a therapeutically effective amount of an active agent selected from an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequesterant, an LDL receptor inducer, vitamin $B_6$ and the pharmaceutically acceptable salts thereof, vitamin $B_{12}$, aspirin, a beta-blocker, vitamin C, vitamin E and beta carotene.

15. A method for preventing or reducing the risk of occurrence, or recurrence where the potential exists, of an atherosclerotic disease event comprising the administration of a therapeutically effective amount of an HMG-CoA reductase inhibitor in combination with folic acid or a pharmaceutically acceptable salt or ester thereof to a person at risk of having an atherosclerotic disease event.

16. The method of claim 15 wherein the person receiving the administration has atherosclerotic disease.

17. The method of claim 15 wherein the person receiving the administration is at risk of developing atherosclerotic disease.

18. The method of claim 15 wherein the atherosclerotic disease event is selected from a coronary heart disease event, a cerebrovascular event and intermittent claudication.

19. The method of claim 18 wherein the coronary heart disease event is selected from coronary heart disease death, myocardial infarction, and coronary revascularization procedures.

20. The method of claim 18 wherein the cerebrovascular event is selected from a cerebrovascular accident and a transient ischemic attack.

21. The method of claim 15 wherein the HMG-CoA reductase inhibitor is selected from lovastatin, simvastatin, pravastatin, fluvastatin, atorvastatin, rivastatin and the pharmaceutically acceptable salts and esters thereof.

22. The method of claim 21 wherein the HMG-CoA reductase inhibitor is selected from lovastatin and simvastatin.

23. The method of claim 15 wherein the pharmaceutically acceptable salt of folic acid is selected from the sodium salt and the methylglucamine salt.

24. The method of claim 15 further comprising the administration of a therapeutically effective amount of an active agent selected from HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequesterant, an LDL receptor inducer, vitamin $B_6$ and the pharmaceutically acceptable salts thereof, vitamin $B_{12}$, aspirin, a beta-blocker, vitamin C, vitamin E and beta carotene.

25. A pharmaceutical composition comprising a therapeutically effective amount of an HMG-CoA reductase inhibitor, a therapeutically effective amount of folic acid or a pharmaceutically acceptable salt or ester thereof, and a pharmaceutically acceptable carrier.

26. The composition of claim 25 wherein the HMG-CoA reductase inhibitor is selected from lovastatin, simvastatin, pravastatin, fluvastatin, atorvastatin, rivastatin and the pharmaceutically acceptable salts and esters thereof.

27. The composition of claim 26 wherein the HMG-CoA reductase inhibitor is selected from lovastatin and simvastatin.

28. The composition of claim 25 wherein the pharmaceutically acceptable salt of folic acid is selected from the sodium salt and the methylglucamine salt.

29. The composition of claim 25 further comprising a therapeutically effective amount of an active agent selected from an HMG-CoA synthase inhibitor, a squalene epoxidase inhibitor, a squalene synthetase inhibitor, an ACAT inhibitor, probucol, niacin, a fibrate, a cholesterol absorption inhibitor, a bile acid sequesterant, an LDL receptor inducer, vitamin $B_6$ and the pharmaceutically acceptable salts thereof, vitamin $B_{12}$, aspirin, a beta-blocker, vitamin C, vitamin E and beta carotene.

* * * * *